(12) United States Patent
Rutenberg et al.

(10) Patent No.: US 9,248,137 B2
(45) Date of Patent: Feb. 2, 2016

(54) COMPOSITIONS AND METHODS FOR ALLEVIATING SYMPTOMS ASSOCIATED WITH PERIMENOPAUSAL AND/OR MENOPAUSAL DISORDER OR DISCOMFORT

(71) Applicant: Lipogen Ltd., Haifa (IL)

(72) Inventors: David Rutenberg, Haifa (IL); Rina Perry Faierwerger, Moshav Bat Shlomo (IL)

(73) Assignee: Lipogen Ltd., Haifa (IL)

( * ) Notice: Subject to any disclaimer, the term of this patent is extended or adjusted under 35 U.S.C. 154(b) by 0 days.

(21) Appl. No.: 14/632,005

(22) Filed: Feb. 26, 2015

(65) Prior Publication Data

US 2015/0164925 A1 Jun. 18, 2015

Related U.S. Application Data

(63) Continuation-in-part of application No. 13/773,653, filed on Feb. 22, 2013, which is a continuation-in-part of application No. 12/606,975, filed on Oct. 27, 2009, now Pat. No. 8,399,432.

(51) Int. Cl.

| | | |
|---|---|---|
| *A61K 31/66* | (2006.01) | |
| *A61K 31/661* | (2006.01) | |
| *A61K 33/06* | (2006.01) | |
| *A61K 33/08* | (2006.01) | |
| *A23L 1/304* | (2006.01) | |
| *A23L 1/30* | (2006.01) | |

(52) U.S. Cl.
CPC .............. *A61K 31/661* (2013.01); *A23L 1/304* (2013.01); *A23L 1/3008* (2013.01); *A61K 33/06* (2013.01); *A61K 33/08* (2013.01)

(58) Field of Classification Search
CPC ....... A61K 33/08; A23L 1/304; A23L 1/3008
USPC ......................................................... 514/120
See application file for complete search history.

(56) References Cited

U.S. PATENT DOCUMENTS 5,424,331 A * 6/1995 Shlyankevich ............... 514/456
6,051,564 A * 4/2000 Shenfeld et al. ............. 514/120

OTHER PUBLICATIONS

Carranza-Lira et al., Maturitas, 2003;45:55-58.*
Christie, William W., Phosphatidylserine and Related Lipids, James Hutton Institute, Scotland (2013), lipidlibrary.aocs.org.
Omori, T., et al, The Distribution of Phosphatidyl-D-Serine in the Rat, Biosci. Biotechnical. Biochem., 74 (9), 1953-1955, 2010.
Montane, J. L., et al, Cyclic changes in phospholipid content and composition in human endometrium during the menstrual cycle, J. Reprod. Fert. (1985) 73 317-321.
Hellhammer, J., et al, A soy-based phosphatidylserine/ phosphatidic acid comples (PAS) normalizes the stress reactivity of hypothalamus-pituitary-adernal-axis in chronocally stressed male subjects: a randomized, placebo-controlled study, Lipids in Health and Disease 2014, 13:121.
Freeman, E. W., et al, Premenstrual Syndrome as a Predictor of Menopausal Symptoms, Lippincott Williams & Wilkins, vol. 103, No. 5, part 1, 2004.
Wikipedia Page on PA (Phosphatidic acids), http://en.wikipedia.org/wiki/Phosphatidic_acid.

* cited by examiner

*Primary Examiner* — San-Ming Hui
(74) *Attorney, Agent, or Firm* — Reuven K. Mouallem, Esq.; FlashPoint IP Ltd.

(57) ABSTRACT

The present invention discloses pharmaceutical/nutritional compositions and methods for alleviating symptoms associated with perimenopausal and/or menopausal disorder or discomfort. The methods include the step of administering, to a subject in need thereof, an effective amount of a composition including at least 2% (w/w) phosphatidic acid, or salts thereof, out of the total effective composition, as a first effective ingredient for alleviating at least one discomfort symptom. Preferably, the composition further includes a suitable amount of at least one bio-available form of magnesium as a second effective ingredient. Preferably, at least one bio-available form is selected from the group consisting of: magnesium oxide, magnesium citrate, magnesium hydroxide, magnesium stearate, and a magnesium salt of the phosphatidic acid. Preferably, the step of administering is performed in a multi-part regimen, and is performed by at least one delivery method selected from the group consisting of: oral delivery and intravenous delivery.

11 Claims, No Drawings

COMPOSITIONS AND METHODS FOR ALLEVIATING SYMPTOMS ASSOCIATED WITH PERIMENOPAUSAL AND/OR MENOPAUSAL DISORDER OR DISCOMFORT

CROSS REFERENCE TO RELATED APPLICATIONS

This patent application is a continuation-in-part (CIP) of, and claims priority to, U.S. patent application Ser. No. 13/773,653, filed on Feb. 22, 2013, which therein claims priority to U.S. patent application Ser. No. 12/606,975, filed on Oct. 27, 2009, and which are hereby incorporated by reference in their entirety.

FIELD AND BACKGROUND OF THE INVENTION

The present invention relates to compositions and methods for alleviating symptoms associated with perimenopausal and/or menopausal disorder or discomfort.

While Phosphatidyl-L-serine (PS) has been implicated in treatments for premenstrual syndrome (PMS) (alone and in conjunction with phosphatidic acid (PA)), as well as for cognitive disorders such as stress, very little has been shown regarding PA monotherapy treatments. PA was shown to be effective in treating PMS both alone and in conjunction with bio-available magnesium.

Recently, studies have substantiated that there is a synergistic mechanism by which PS and PA (the combination referred to herein as PAS) operate with regard to stress reactivity in men (see Hellhammer et al., *Lipids in Health and Disease*, 2014, 13, 121). Chronic stress has been shown to reduce cortisol binding globulin (CBG)—a glycoprotein synthesized in the liver, and secreted in the blood which binds with a high affinity, but low capacity, in the blood to glucocorticoid hormones, such as cortisol in humans and corticosterone in laboratory rodents. A drop of CBG in chronically-stressed subjects was hypothesized therein to explain that PAS first causes a normalization of CBG levels under such conditions, which then result in a normalization of the activity and reactivity of the HPAA (Hypothalamic-Pituitary-Adrenal Axis).

PS and PA, while both being phospholipids, have distinct physicochemical properties which lead to divergent physiological behavior. With regard to the distribution of PLs in the human body, it is widely known that PS is concentrated primarily in the brain as well as to some extent in the central nervous system (CNS), while PA in contrast is distributed throughout the body (see "The Distribution of Phosphatidyl-D-serine in the Rat" by Omori et al. *Biosci. Biotechnol. Biochem.*, 2010, 74(9), 1953-1955; and "Phosphatidylserine: structure, occurrence, biochemistry and analysis" by Christie, *AOCS Lipid Library*, http://lipidlibrary.aocs.org/Lipids/ps/index.htm, 2013).

Via hydrolysis, many PLs serve as precursors to important biochemical agents in the body. For example, PC is known to release choline which acts as a precursor for production of acetylcholine, a known neurotransmitter. Similarly, PS releases L-serine in the brain which undergoes conversion to D-serine via an isomerase racemase (an isomerase enzyme which catalyzes the stereochemical inversion around the asymmetric carbon atom in biological molecules having only one center of asymmetry). D-serine has been implicated in many physiological and neurological therapeutic remedies.

Under physiological conditions, serine binds phosphate through its free hydroxyl (—OH) group to form the phosphate ester of PS. The head group of PS has three charged groups: a positively-charged primary amine, a partially negatively-charged carboxyl group, and a negatively-charged phosphate group. Thus, PS has a net negative charge in equilibrium due to its carboxylate group. In PA, two free hydroxyl groups are available for ionization. The first hydroxyl group is readily ionized in equilibrium at a pH greater than 2. The second hydroxyl group is predominantly ionized in equilibrium at a pH typical of physiological environments.

While PA is known to undergo cleavage of its beta-position fatty acid to form lysophosphatidic acid (LPA, an important implicated precursor), the double negative charge of the phosphate group of PA as explained above stands out in stark contrast to all other PLs, including PS, which have less negatively-charged phosphate moieties. Such physicochemical properties make PA impermeable in the brain (i.e., the so-called Blood-Brain Barrier (BBB) separating circulating blood from the brain extracellular fluid (BECF) in the CNS) (see article on "Phosphatidic Acid," Wikipedia, http://en.wikipedia.org/wiki/Phosphatidic_acid).

A scientific publication by Montané and Pérez-Balllester (*J. Reprod. Fert.*, 1985, 73, 317-321) on "Cyclic changes in phospholipid content and composition in human endometrium during the menstrual cycle" states, "A significant increase in total phospholipid content of the endometrium took place during the secretory phase of the human menstrual cycle (26% increase from mid-proliferative to premenstrual stage). The major phospholipid, phosphatidylcholine, was increased by 30%, whereas phosphatidylethanolamine was unchanged. Phosphatidyl-serine and -inositol underwent the largest percentage increases (40%). Phosphatidic acid levels were the only ones to decrease (−52%), a finding consistent with the role of this lipid as precursor of the increased phospholipids."

The statements above indicate that human cyclic changes in phospholipid content during a women's PMS phase predominantly concern PS, PI, and PC (PE showed zero change). PC, PI, and PE are readily available in normal diets, and therefore are excluded from attribution of any therapeutic effects. However, PS and PA are not readily available in normal diets. The fact that the PA levels decreased dramatically during the menstrual-cycle study stands in sharp contrast to the increase observed in the PS levels. Thus, it would not be considered a reasonable assumption to extrapolate the effectivity of PS to PA in the treatment of PMS.

PMS has been shown (see Freeman et al., *Obstetrics and Gynecology*, May 2004, 103, 960-965) to have a direct correlation with menopause in the sense that women who suffer from PMS symptoms have a high likelihood of suffering later in life during the transition to menopause (known as perimenopause) as well.

With regard to magnesium, it is estimated that the binding of Mg (as $Mg^{2+}$) to PA is at least ten times stronger than Mg to PS. Thus, in the presence of PS and PA, Mg would be expected to preferentially bind to PA; in isolation (i.e., given only PA and Mg), PA would be expected to scavenge and selectively bind any bio-available Mg.

It would be desirable to have compositions and methods for alleviating symptoms associated with perimenopausal and/or menopausal disorder and discomfort.

SUMMARY OF THE INVENTION

It is the purpose of the present invention to provide compositions and methods for alleviating symptoms associated with perimenopausal and/or menopausal disorder or discomfort.

Furthermore, it is noted that the term "exemplary" is used herein to refer to examples of embodiments and/or implementations, and is not meant to necessarily convey a more-desirable use-case. Similarly, the term "preferred" is used herein to refer to an example out of an assortment of contemplated embodiments and/or implementations, and is not meant to necessarily convey a more-desirable use-case. Therefore, it is understood from the above that "exemplary" and "preferred" may be applied herein to multiple embodiments and/or implementations.

Embodiments of the present invention provide compositions and methods, for decreasing menopause symptoms, including phosphatidic acid and, optionally, a bio-available form of magnesium. Such compositions are administrable via intravenous or oral administration. Such compositions can also include other excipients (e.g., additional phospholipids, lyso-phospholipids, sugars, and proteins) to prepare capsules, tablets, and granules with improved handling and shelf life. Because of the absence of any safety problem, such compositions can be blended into daily foods and beverages, either in powder or liquid form, or as a hydrogenated substance for use in decreasing menopause symptoms. Embodiments of the present invention further provide compositions and methods including phosphatidic acid.

Therefore, according to the present invention, there is provided for the first time a pharmaceutical/nutritional composition for use in alleviating symptoms associated with perimenopausal and/or menopausal disorder or discomfort, the pharmaceutical/nutritional composition including: (a) at least 2% (w/w) phosphatidic acid, or salts thereof, out of the total effective composition, as a first effective ingredient for alleviating at least one discomfort symptom.

Preferably, at least one discomfort symptom is selected from the group consisting of: acne, breast swelling, breast tenderness, tiredness/fatigue, insomnia, upset stomach/stomach aches, bloating, constipation, diarrhea, headaches, backaches, appetite changes, food cravings, joint pain, muscle pain, and changes in regular behavior, night sweats, cold flashes, atherosclerosis, migraines, rapid heartbeat, dysfunctional bleeding, vaginal atrophy, vaginal itching, vaginal dryness, watery vaginal discharge, increased urinary frequency, urinary incontinence, urinary urgency, vaginal candidiasis, urinary tract infections, osteopenia, breast atrophy, decreased skin elasticity, formication, skin thinning, skin dryness, fatigue, irritability, memory loss, mood disturbance, sleep disturbances, insomnia, painful intercourse, decreased libido, and problems reaching orgasm.

Preferably, the pharmaceutical/nutritional composition further includes: (b) a suitable amount of at least one bio-available form of magnesium as a second effective ingredient.

Most preferably, at least one discomfort symptom is selected from the group consisting of: acne, breast swelling, breast tenderness, tiredness/fatigue, insomnia, upset stomach/stomach aches, bloating, constipation, diarrhea, headaches, backaches, appetite changes, food cravings, joint pain, muscle pain, and changes in regular behavior, night sweats, cold flashes, atherosclerosis, migraines, rapid heartbeat, dysfunctional bleeding, vaginal atrophy, vaginal itching, vaginal dryness, watery vaginal discharge, increased urinary frequency, urinary incontinence, urinary urgency, vaginal candidiasis, urinary tract infections, osteopenia, breast atrophy, decreased skin elasticity, formication, skin thinning, skin dryness, fatigue, irritability, memory loss, mood disturbance, sleep disturbances, insomnia, painful intercourse, decreased libido, and problems reaching orgasm.

Most preferably, at least one bio-available form is selected from the group consisting of: magnesium oxide, magnesium citrate, magnesium hydroxide, and magnesium stearate.

Most preferably, at least one bio-available form is a magnesium salt of the phosphatidic acid.

Preferably, the pharmaceutical/nutritional composition further includes: (b) a pharmaceutical excipient.

Preferably, the pharmaceutical/nutritional composition further includes: (b) a nutritional excipient.

Preferably, the total effective composition is administrable in a multi-part regimen.

Preferably, the total effective composition is administrable by at least one delivery method selected from the group consisting of: oral delivery and intravenous delivery.

According to the present invention, there is provided for the first time a method for use in alleviating symptoms associated with perimenopausal and/or menopausal disorder or discomfort, the method including the step of: (a) administering, to a subject in need thereof, an effective amount of a pharmaceutical/nutritional composition including: (i) at least 2% (w/w) phosphatidic acid, or salts thereof, out of a total composition, as an effective ingredient for alleviating at least one discomfort symptom.

Preferably, at least one discomfort symptom is selected from the group consisting of: acne, breast swelling, breast tenderness, tiredness/fatigue, insomnia, upset stomach/stomach aches, bloating, constipation, diarrhea, headaches, backaches, appetite changes, food cravings, joint pain, muscle pain, and changes in regular behavior, night sweats, cold flashes, atherosclerosis, migraines, rapid heartbeat, dysfunctional bleeding, vaginal atrophy, vaginal itching, vaginal dryness, watery vaginal discharge, increased urinary frequency, urinary incontinence, urinary urgency, vaginal candidiasis, urinary tract infections, osteopenia, breast atrophy, decreased skin elasticity, formication, skin thinning, skin dryness, fatigue, irritability, memory loss, mood disturbance, sleep disturbances, insomnia, painful intercourse, decreased libido, and problems reaching orgasm.

Preferably, the total pharmaceutical/nutritional composition further includes: (ii) a suitable amount of at least one bio-available form of magnesium as a second effective ingredient.

Most preferably, at least one discomfort symptom is selected from the group consisting of: acne, breast swelling, breast tenderness, tiredness/fatigue, insomnia, upset stomach/stomach aches, bloating, constipation, diarrhea, headaches, backaches, appetite changes, food cravings, joint pain, muscle pain, and changes in regular behavior, night sweats, cold flashes, atherosclerosis, migraines, rapid heartbeat, dysfunctional bleeding, vaginal atrophy, vaginal itching, vaginal dryness, watery vaginal discharge, increased urinary frequency, urinary incontinence, urinary urgency, vaginal candidiasis, urinary tract infections, osteopenia, breast atrophy, decreased skin elasticity, formication, skin thinning, skin dryness, fatigue, irritability, memory loss, mood disturbance, sleep disturbances, insomnia, painful intercourse, decreased libido, and problems reaching orgasm.

Most preferably, at least one bio-available form is selected from the group consisting of: magnesium oxide, magnesium citrate, magnesium hydroxide, and magnesium stearate.

Most preferably, at least one bio-available form is a magnesium salt of the phosphatidic acid.

Preferably, the pharmaceutical/nutritional composition further includes: (ii) a pharmaceutical excipient.

Preferably, the pharmaceutical/nutritional composition further includes: (ii) a nutritional excipient.

Preferably, the step of administering is performed in a multi-part regimen.

Preferably, the step of administering is performed by at least one delivery method selected from the group consisting of: oral delivery and intravenous delivery.

These and further embodiments will be apparent from the detailed description and examples that follow.

DESCRIPTION OF THE PREFERRED EMBODIMENTS

The present invention relates to compositions and methods for alleviating symptoms associated with perimenopausal and/or menopausal disorder or discomfort. The aspects, uses, and advantages for such compositions and methods, according to the present invention, may be better understood with reference to the accompanying description. Exemplary embodiments of the present invention are detailed below in the following exemplary formulations.

Pharmaceutical/nutritional compositions for alleviating symptoms associated with menopausal disorder or discomfort were formulated using effective amounts of phosphatidic acid and, optionally, at least one bio-available form of magnesium.

Exemplary Formulaton A:

Phosphatidic acid (PA) was prepared by Lipogen Products (9000) Ltd. via a process of enzymatic reaction from a substrate soybean lecithin. 400 g. of PA was used to produce the formulation.

Exemplary Formulation B:

PA was prepared by Lipogen Products (9000) Ltd. as in Formulation A. Magnesium citrate (Dr. Paul Lohmann GmbH KG) was used as a bio-available form of magnesium. 400 g. of PA was combined with 10 g. of magnesium citrate to produce the formulation.

Exemplary Formulation C:

PA was prepared by Lipogen Products (9000) Ltd. as in Formulation A. Magnesium oxide (Dr. Paul Lohmann GmbH KG) was used as a bio-available form of magnesium. 400 g. of PA was combined with 10 g. of magnesium oxide to produce the formulation.

Exemplary Formulation D:

PA was prepared by Lipogen Products (9000) Ltd as in Formulation A. PA was then converted into a magnesium salt by ion exchange with magnesium chloride (Dr. Paul Lohmann GmbH KG). The magnesium salt of PA (PA-Mg) was used as a bio-available form of magnesium. 400 g. of PA-Mg was used to produce the formulation.

Results:

The effect of alleviating perimenopause and/or menopause symptoms via oral administration was investigated in the following experiments. In studies involving PA and PA/Mg formulations, the results are presented relative to the studies non-treatment (i.e., no therapeutic indication).

The menopause symptom scale used was based on an assessment by the subject. Examples of the perimenopause and/or menopause physical symptoms include acne, breast swelling, breast tenderness, tiredness/fatigue, insomnia, upset stomach/stomach aches, bloating, constipation, diarrhea, headaches, backaches, appetite changes, food cravings, joint pain, muscle pain, and changes in regular behavior, night sweats, cold flashes, atherosclerosis, migraines, rapid heartbeat, dysfunctional bleeding, vaginal atrophy, vaginal itching, vaginal dryness, watery vaginal discharge, increased urinary frequency, urinary incontinence, urinary urgency, vaginal candidiasis, urinary tract infections, osteopenia, breast atrophy, decreased skin elasticity, formication, skin thinning, skin dryness, painful intercourse, decreased libido, and problems reaching orgasm.

The perimenopause and/or menopause behavioral symptoms include any changes that the subjects noticed in everyday behavior. Examples of the perimenopause and/or menopause behavioral symptoms include feelings of deep sadness or despair, feelings of intense tension or anxiety, increased intense sensitivity to rejection or criticism, panic attacks, rapid and severe mood swings, uncontrollable crying, lasting irritability or anger, apathy, difficulty concentrating, chronic fatigue, insomnia or hypersomnia, irritability, memory loss, mood disturbance, sleep disturbances, feeling overwhelmed, feeling out of control, change in sex drive, and increased need for emotional closeness.

Classification of the subjects as suffering from perimenopausal and/or menopausal disorder or discomfort was based on the presence of longer, irregular, and/or absent menstruation cycles as reported by the subjects during a pre-screening stage.

The results correlate to the following subjective ranking: "✓"=comparable improvement to no treatments, "*"=slight improvement over no treatment, and "**"=large improvement over no treatment.

Formulation A: Seven female volunteers who normally suffer from perimenopausal and/or menopausal disorder or discomfort received 100 mg. of Formulation A four times per day from three weeks before the expected monthly menstruation until the commencement of menstruation (Treatment A). The results are presented in Table 1. As indicated in Table 1, a significant improvement was observed in all seven participants.

TABLE 1

The effect of alleviating perimenopause and/or menopause symptoms using a PA treatment in an initial treatment-regimen experiment.

| Subject age (suffering from perimenopausal/ menopausal disorder/ discomfort) | Physical symptoms with Treatment A | Behavioral symptoms with Treatment A | Cumulative symptoms with Treatment A |
|---|---|---|---|
| 42 | * | ✓ | * |
| 45 | * | ** | ** |
| 49 | * | ** | ** |
| 41 | * | * | * |
| 45 | * | * | ** |
| 50 | * | * | * |
| 48 | * | * | * |

After one menstruation cycle after the menstruation date of the study in Table 1, the same seven females who participated reported that after cessation of the treatment, their usual symptoms reappeared. The above seven female then received 100 mg. of Formulation A four times per day from three weeks before the expected monthly menstruation until the commencement of menstruation (Treatment A). The results are presented in Table 2. As indicated in Table 1, a significant improvement was observed in all seven participants.

TABLE 2

The effect of alleviating perimenopause and/or menopause symptoms using a PA treatment in a secondary treatment-regimen experiment after the re-emergence of symptoms.

| Subject age (suffering from perimenopausal/ menopausal disorder or discomfort) | Physical symptoms with Treatment A | Behavioral symptoms with Treatment A | Cumulative symptoms with Treatment A |
|---|---|---|---|
| 42 | ** | ✓ | ** |
| 45 | * | ** | ** |
| 49 | * | ** | ** |
| 41 | * | ✓ | * |
| 45 | * | * | ** |
| 50 | * | * | * |
| 48 | * | ✓ | * |

Formulation B: Seven female volunteers who normally suffer from perimenopausal and/or menopausal disorder or discomfort received 150 mg. of Formulation B four times per day from three weeks before the expected monthly menstruation until the commencement of menstruation (Treatment B). The results are presented in Table 3. As indicated in Table 3, a significant improvement was observed in all seven participants.

TABLE 3

The effect of alleviating perimenopause and/or menopause symptoms using a PA/Mg citrate treatment in an initial treatment-regimen experiment.

| Subject age (suffering from perimenopausal/ menopausal disorder or discomfort) | Physical symptoms with Treatment B | Behavioral symptoms with Treatment B | Cumulative symptoms with Treatment B |
|---|---|---|---|
| 42 | * | ✓ | * |
| 45 | * | ** | ** |
| 49 | ** | ** | ** |
| 41 | * | * | * |
| 45 | * | * | ** |
| 50 | ** | * | ** |
| 48 | * | ** | ** |

Formulation C: Seven female volunteers who normally suffer from perimenopausal and/or menopausal disorder or discomfort received 150 mg. of Formulation C four times per day from three weeks before the expected monthly menstruation until the commencement of menstruation (Treatment C). The results are presented in Table 4. As indicated in Table 4, a significant improvement was observed in all seven participants.

TABLE 4

The effect of alleviating perimenopause and/or menopause symptoms using a PA/Mg oxide treatment in an initial treatment-regimen experiment.

| Subject age (suffering from perimenopausal/ menopausal disorder or discomfort) | Physical symptoms with Treatment C | Behavioral symptoms with Treatment C | Cumulative symptoms with Treatment C |
|---|---|---|---|
| 42 | ** | ✓ | ** |
| 45 | * | ** | ** |
| 49 | ** | ** | ** |
| 41 | * | ** | * |
| 45 | ** | * | ** |
| 50 | ** | ** | ** |
| 48 | ** | * | ** |

Formulation D: Seven female volunteers who normally suffer from perimenopausal and/or menopausal disorder or discomfort received 100 mg. of Formulation D four times per day from three weeks before the expected monthly menstruation until the commencement of menstruation (Treatment D). The results are presented in Table 5. As indicated in Table 5, a significant improvement was observed in all seven participants.

TABLE 5

The effect of alleviating perimenopause and/or menopause symptoms using a PA-Mg complex treatment in an initial treatment-regimen experiment.

| Subject age (suffering from perimenopausal/ menopausal disorder or discomfort) | Physical symptoms with Treatment D | Behavioral symptoms with Treatment D | Cumulative symptoms with Treatment D |
|---|---|---|---|
| 42 | * | * | * |
| 45 | ** | ** | ** |
| 49 | * | ** | ** |
| 41 | * | * | * |
| 45 | ** | * | ** |
| 50 | ** | * | * |
| 48 | ** | * | ** |

The treatments can be continuously and readily administered with no pain because the PA and Mg supplied in the compositions described above are freely ingested.

While the present invention has been described with respect to a limited number of embodiments, it will be appreciated that many variations, modifications, and other applications of the present invention may be made.

What is claimed is:

1. A method for use in alleviating symptoms associated with perimenopausal and/or menopausal disorder or discomfort, the method comprising the step of:
   (a) administering, to a subject in need thereof, an effective amount of a pharmaceutical/nutritional composition including:
      (i) at least 2% (w/w) phosphatidic acid, or salts thereof, out of a total composition, as an effective ingredient for alleviating at least one discomfort symptom, wherein said at least one discomfort symptom is selected from the group consisting of: acne, breast swelling, breast tenderness, tiredness/fatigue, insomnia, upset stomach/stomach aches, bloating, constipation, diarrhea, headaches, backaches, appetite changes, food cravings, joint pain, muscle pain, cold flashes, breast atrophy.

2. The method of claim 1, wherein said pharmaceutical/nutritional composition further includes:
   (ii) a suitable amount of at least one bio-available form of magnesium as a second effective ingredient.

3. The method of claim 2, wherein said at least one bioavailable form is selected from the group consisting of: magnesium oxide, magnesium citrate, magnesium hydroxide, and magnesium stearate.

4. The method of claim 2, wherein said at least one bioavailable form is a magnesium salt of said phosphatidic acid.

5. The method of claim 1, wherein said pharmaceutical/nutritional composition further includes:
(ii) a pharmaceutical excipient.

6. The method of claim 1, wherein said pharmaceutical/nutritional composition further includes:
(ii) a nutritional excipient.

7. The method of claim 1, wherein said step of administering is performed in a multi-part regimen.

8. The method of claim 1, wherein said step of administering is performed by at least one delivery method selected from the group consisting of: oral delivery and intravenous delivery.

9. The method of claim 1, wherein said at least one discomfort symptom is further selected from the group consisting of: migraines and rapid heartbeat.

10. The method of claim 9, wherein said at least one discomfort symptom further includes sleep disturbance.

11. The method of claim 9, wherein said at least one discomfort symptom is further selected from the group consisting of: changes in regular behavior, irritability, and mood disturbance.

* * * * *